(12) United States Patent
Boiteau et al.

(10) Patent No.: US 9,908,948 B2
(45) Date of Patent: Mar. 6, 2018

(54) ENANTIOPURE OR ENANTIOENRICHED BDDE AND ITS USE AS CROSSLINKING AGENT IN THE MANUFACTURE OF CROSS-LINKED PRODUCTS

(71) Applicant: GALDERMA S.A., Cham (CH)

(72) Inventors: Jean-Guy Boiteau, Valbonne (FR); Lars Nord, Uppsala (SE); Thibaut Gerfaud, Mouans Sartoux (FR)

(73) Assignee: GALDERMA S.A., Cham (CH)

( * ) Notice: Subject to any disclaimer, the term of this patent is extended or adjusted under 35 U.S.C. 154(b) by 0 days.

(21) Appl. No.: 15/507,029

(22) PCT Filed: Aug. 28, 2015

(86) PCT No.: PCT/EP2015/069771
§ 371 (c)(1),
(2) Date: Feb. 27, 2017

(87) PCT Pub. No.: WO2016/030516
PCT Pub. Date: Mar. 3, 2016

(65) Prior Publication Data
US 2017/0291963 A1    Oct. 12, 2017

Related U.S. Application Data

(60) Provisional application No. 62/043,683, filed on Aug. 29, 2014.

(51) Int. Cl.
| | |
|---|---|
| *A61K 31/728* | (2006.01) |
| *C08B 37/08* | (2006.01) |
| *C07D 303/27* | (2006.01) |
| *C07D 303/24* | (2006.01) |
| *C07D 301/03* | (2006.01) |
| *C07C 29/10* | (2006.01) |

(52) U.S. Cl.
CPC .......... *C08B 37/0072* (2013.01); *C07C 29/10* (2013.01); *C07D 301/03* (2013.01); *C07D 303/24* (2013.01); *C07D 303/27* (2013.01)

(58) Field of Classification Search
CPC .. C07D 303/27; C07D 301/03; C07D 303/24; A61K 31/728; C08B 37/0072; C07C 29/10
USPC .......................................................... 549/555
See application file for complete search history.

(56) References Cited

U.S. PATENT DOCUMENTS 3,096,349 A * 7/1963 Meyer et al. ........ C07D 303/24
528/418
2003/0094719 A1   5/2003 Yang et al.

FOREIGN PATENT DOCUMENTS

| WO | WO 97/04012 A1 | 2/1997 |
| WO | WO 2012/054301 A1 | 4/2012 |
| WO | WO 2013/021249 A1 | 2/2013 |

OTHER PUBLICATIONS

Hoye; Synlett 1996, 615-616.*

(Continued)

*Primary Examiner* — Daniel R Carcanague
(74) *Attorney, Agent, or Firm* — Buchanan Ingersoll & Rooney P.C.

(57) ABSTRACT

Enantiomers of butanediol diglycidyl ether (BDDE) are present in an enantiomerically enriched enantioenriched mixture of BDDE stereisomers or in an enantiomerically pure BDDE. Enantiomerically enriched or pure BDDE is useful as a cross-linking agent, such as in the preparation of a cross-linked hyaluronic acid product.

7 Claims, 7 Drawing Sheets

Enantiopure (R,R) BDDE crosslinked HA

Enantiopure (S,S) BDDE crosslinked HA

Racemic BDDE crosslinked HA

----- Meso BDDE
----- (S,S) BDDE
----- (R,R) BDDE
⌒ HA

(56) References Cited

OTHER PUBLICATIONS

International Search Report (PCT/ISA/210) dated Nov. 11, 2015, by the European Patent Office as the International Searching Authority for International Application No. PCT/EP2015/069771.
Written Opinion (PCT/ISA/237) dated Nov. 11, 2015, by the European Patent Office as the International Searching Authority for International Application No. PCT/EP2015/069771.
Schaus et al., "Highly Selective Hydrolytic Kinetic Resolution of Terminal Epoxides Catalyzed by Chiral (salen)Co Complexes. Practical Synthesis of Enantioenriched Terminal Epoxides and 1,2-Diols", Journal of the American Chemical Society, Jan. 2002, pp. 1307-1315, vol. 124, No. 7.
De Boulle et al., "A Review of the Metabolism of 1,4-Butanediol Diglycidyl Ether—Crosslinked Hyaluronic Acid Dermal Fillers", Mini Review Article, Dec. 2013, pp. 1758-1766.
Kenne et al., "Modification and cross-linking parameters in hyaluronic acid hydrogels—Definitions and analytical methods", Carbohydrate Polymers, 2013, pp. 410-418, vol. 91.
Sall et al., "Comparison of the sensitivity of 11 crosslinked hyaluronic acid gels to bovine testis hyaluronidase", Polymer Degradation and Stability, 2007, pp. 915-919, vol. 92.

\* cited by examiner

Enantiopure (R,R) BDDE
crosslinked HA

Enantiopure (S,S) BDDE
crosslinked HA

Racemic BDDE
crosslinked HA

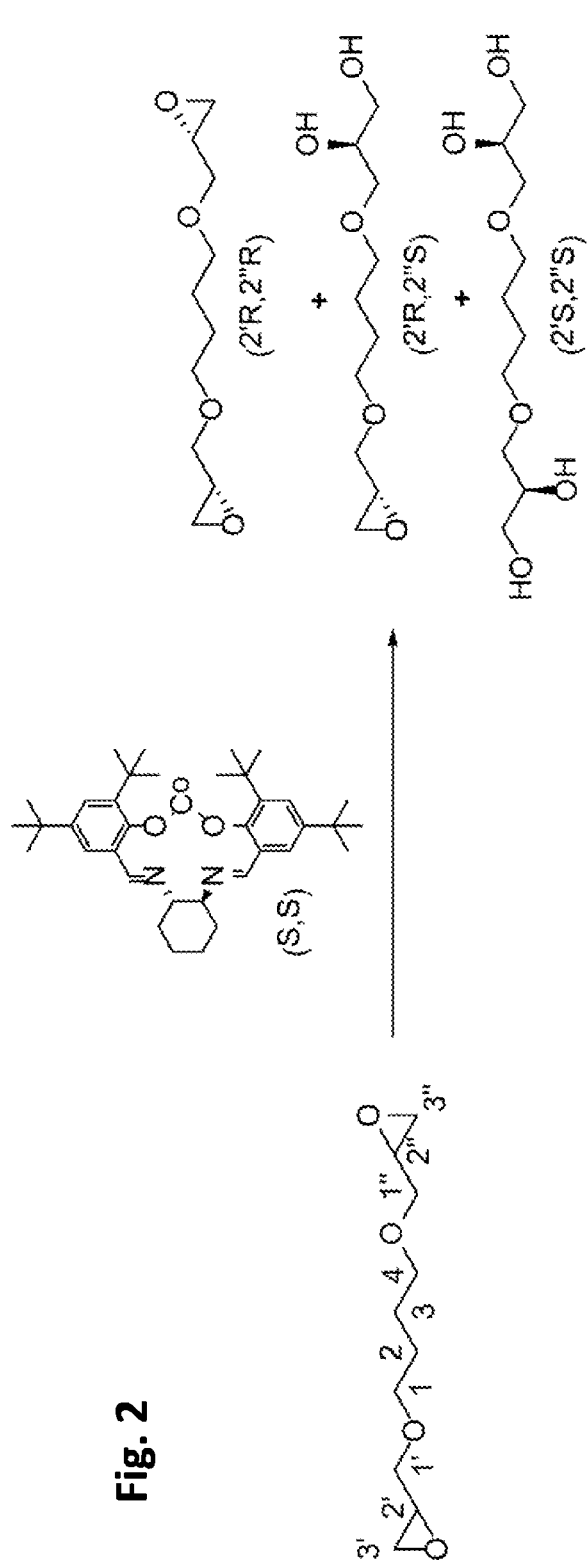
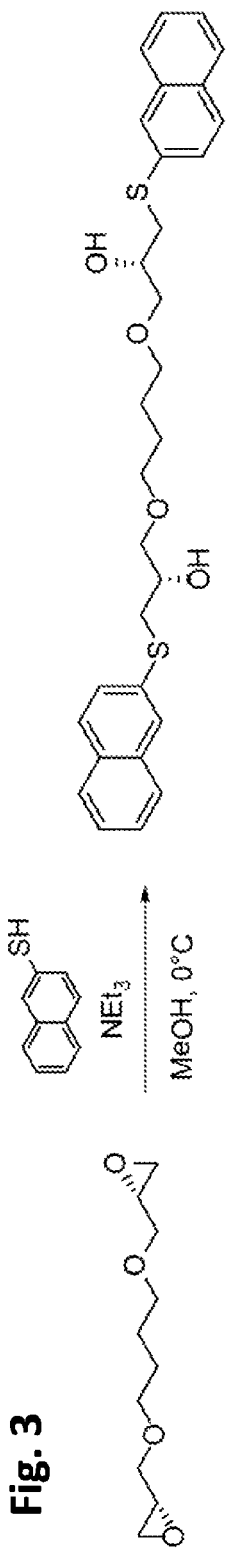
Fig. 2
Fig. 3

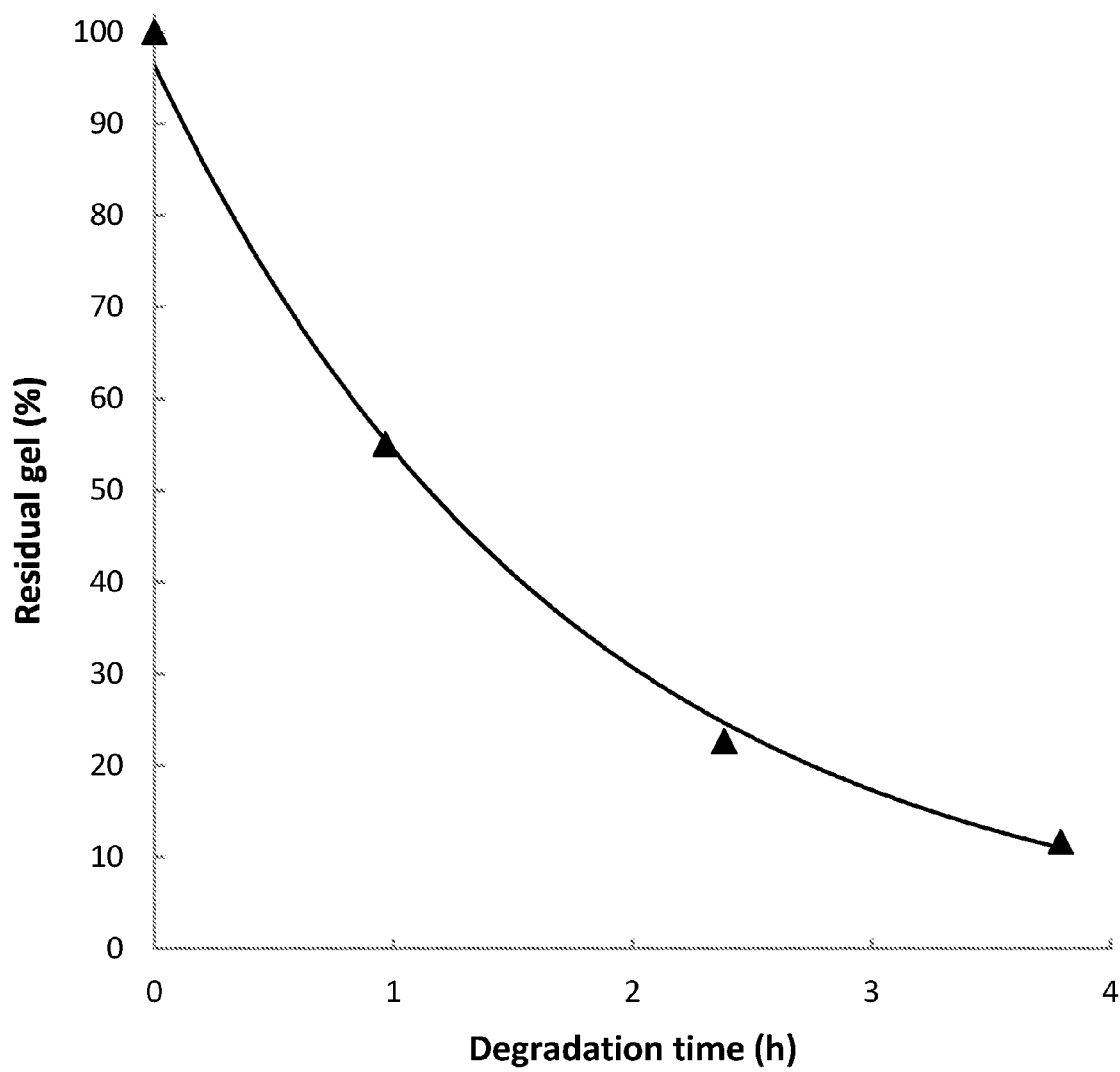

ENANTIOPURE OR ENANTIOENRICHED BDDE AND ITS USE AS CROSSLINKING AGENT IN THE MANUFACTURE OF CROSS-LINKED PRODUCTS

FIELD OF THE INVENTION

The present invention is concerned with enantiomerically pure (enantiopure) or enantiomerically enriched (enantioenriched) butanediol diglycidyl ether (BDDE), also termed 1,4-butanediol diglycidyl ether or 1,4-bis(2,3-epoxypropyloxy)butane and its use as a cross-linking agent in cross-linking reactions. Additionally, the invention concerns cross-linked products obtained by reaction with enantiopure or enantioenriched BDDE, and in particular cross-linked hydrogels obtained by reaction between hyaluronic acid (Hyaluronan or HA) and enantiopure or enantioenriched BDDE.

BACKGROUND OF THE INVENTION

BDDE is the most commonly used homobifunctional epoxide compound. BDDE may react with e.g. amines, acids, hydroxyls and sulfhydryl groups to produce secondary amines, ester, ether or thioether bonds, respectively. BDDE is a cross linking agent used e.g. for preparing amylose, xylan and hydroxyethyl-cellulose; to cross-link polyethylenimine; to cross-link glycosaminoglycans such as hyaluronic acid into hydrogels: for the activation of soluble dextran polymers; and amine or hydroxyl containing bis-epoxy supports are reacted with BDDE to form particles containing terminal epoxide group for immobilization reactions.

Hyaluronic acid consists of a linear unbranched polysaccharide of disaccharide subunits. The subunit is a pair of pyranose sugars, D-Glucuronic acid and N-Acetyl D-Glucosamine, linked by beta 1-3 and beta 1-4 glycosidic bonds. HA can make intra-molecular and inter-molecular interactions by hydrogen bonding. These hydrogen bonds are responsible for the folding of the polysaccharide. Due to its numerous negative charges, HA can retain large amounts of water and acts therefore as a space filler, lubricant and osmotic buffer. However, the poor mechanical properties, rapid degradation and clearance in vivo of soluble hyaluronic acid limit its use as a biomaterial. To improve the mechanical properties and to increase the resistance to degradation by hyaluronidases, HA is chemically modified or cross-linked to form hydrogels. This polysaccharide can e.g. be crosslinked by ether or ester bonds with a diepoxy linker such as BDDE to produce a hydrogel that is composed of a three-dimensional network.

HA is primarily degraded by three different mechanisms: enzymatic degradation, free radical degradation and thermal degradation. Enzymatic degradation is mediated by a large class of enzymes, including endo-glucosidases that breaks down glycosaminoglycans, such as HA, chondroitin or chondroitin sulfate, into smaller fragments which subsequently join the natural elimination process in the body.

SUMMARY OF THE INVENTION

It is an object of the present invention to provide a cross-linked hyaluronic acid product with a modified sensitivity to degradation, and means for manufacturing the product.

It is in particular an object of the present invention to provide a cross-linked hyaluronic acid product with a modified sensitivity to enzymatic degradation, such as by endo-glucosidases, and means for manufacturing the product.

It is a further object of the present invention to provide a cross-linked hyaluronic acid product with a decreased sensitivity to degradation, and means for manufacturing the product.

It is in particular an object of the present invention to provide a cross-linked hyaluronic acid product with a decreased sensitivity to enzymatic degradation, such as by endo-glucosidases, and means for manufacturing the product.

For these and other objects that will be evident from this disclosure, the present invention provides according to a first aspect a compound selected from the following enantiomers of BDDE:

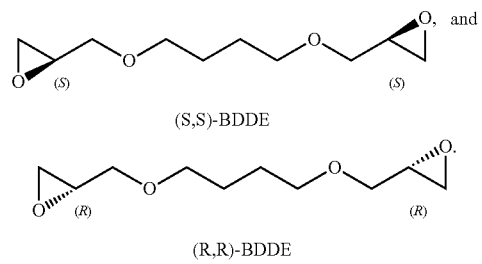

It has surprisingly been realized that the resistance profile towards enzyme degradation of enantiopure or enantioenriched BDDE crosslinked HA is different compared to racemic BDDE crosslinked HA.

In some preferred embodiments, the compound is (S,S)-BDDE. In other preferred embodiments, the compound is (R,R)-BDDE.

According to another aspect, the present invention provides an enantioenriched mixture of BDDE stereisomers, wherein one of the following enantiomers of BDDE is present in a percentage share of at least 50%:

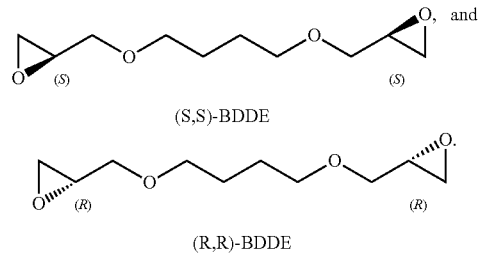

In certain embodiments, the percentage share of the enantioenriched enantiomer is at least 70%, such as at least 80%, such as at least 95%.

According to a related aspect, the present invention provides enantiopure BDDE, consisting of one of the following enantiomers of BDDE:

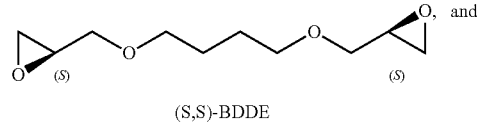

-continued

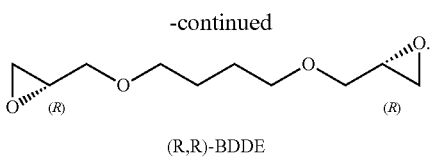

(R,R)-BDDE

In certain embodiments of these aspects, the enantiomer of BDDE is (S,S)-BDDE. In other embodiments of these aspects, the enantiomer of BDDE is (R,R)-BDDE.

According to a related aspect, the present invention provides a process for preparing an enantiopure BDDE or an enantioenriched mixture of BDDE stereisomers, comprising one of the following steps:

stereoselective hydrolysis of racemic BDDE;
alkylation of dibromobutane by enantiopure glycidol;
alkylation of butanediol by enantiopure epichlorohydrine; and
stereoselective epoxidation of butanediol diallyl ether.

According to one aspect, the present invention provides use of an enantioenriched mixture of BDDE stereisomers according to the invention or an enantiopure BDDE according to the invention as a cross-linking agent. In a preferred embodiment, the enantioenriched or enantiopure BDDE is a cross linking agent for a compound selected from the group consisting of amylose, xylan, hydroxyethyl cellulose and dextran; polyethylenimine; glycosaminoglycans, including hyaluronic acid; and amine or hydroxyl containing bis-epoxy supports. A preferred group of compounds are glycosaminoglycans, including heparin, heparan sulfate, chondroitin, chondroitin sulfate, dermatan, dermatan sulfate, keratan, keratan sulfate, and hyaluronic acid, as well as derivatives thereof.

In a preferred embodiment, the use of the enantioenriched mixture of BDDE stereisomers according to the invention or the enantiopure BDDE according to the invention is as a cross-linking agent for hyaluronic acid.

According to an aspect, the present invention provides a cross-linked product selected from the group consisting of cross-linked amylose, xylan, hydroxyethyl cellulose and dextran; polyethylenimine; glycosaminoglycans, including hyaluronic acid; and amine or hydroxyl containing bis-epoxy supports; wherein the product is cross-linked with an enantioenriched mixture of BDDE stereisomers according to the invention, or with an enantiopure BDDE according to the invention. In a preferred embodiment, the cross-linked product is a cross-linked glycosaminoglycan, including heparin, heparan sulfate, chondroitin, chondroitin sulfate, dermatan, dermatan sulfate, keratan, keratan sulfate, and hyaluronic acid, as well as derivatives thereof. In one preferred embodiment, the cross-linked product is a cross-linked hyaluronic acid.

In a preferred embodiment, the cross-linked product is cross-linked via ether bonds to the BDDE. In another preferred embodiment, the cross-linked product is cross-linked via ester bonds to the BDDE. In one preferred embodiment, the cross-linked product is cross-linked via a mixture of ether and ester bonds to the BDDE.

In a preferred embodiment, the cross-linked product is a gel.

In one embodiment, the cross-linked product is a dermal filler product.

According to a related aspect, the present invention provides a process for preparing a cross-linked product according to the invention, comprising the step of cross-linking a compound using an enantioenriched mixture of BDDE stereisomers according to the invention or an enantiopure BDDE according to the invention as cross-linking agent; wherein the compound is selected from the group consisting of amylose, xylan, hydroxyethyl cellulose and dextran; polyethylenimine; glycosaminoglycans, including hyaluronic acid; and amine or hydroxyl containing bis-epoxy supports. In a preferred embodiment, the compound is selected from glycosaminoglycans, including heparin, heparan sulfate, chondroitin, chondroitin sulfate, dermatan, dermatan sulfate, keratan, keratan sulfate, and hyaluronic acid, as well as derivatives thereof. In one preferred embodiment, the compound is hyaluronic acid.

According to one aspect, the present invention provide use of a cross-linked product according to the invention as a medicament or medical device, such as in cosmetic surgery, e.g. dermal filling, body contouring and facial contouring, or in medical surgery, e.g. dermal filling, body contouring, prevention of tissue adhesion, formation of channels, incontinence treatment, and orthopaedic applications. The present invention thus provides a method of treatment of a subject undergoing such cosmetic or medical surgery, involving administration of a cross-linked product according to the invention to a subject in need thereof. The present invention also provides use of a cross-linked product according to the invention for the manufacture of a medicament or a medical device for use in a method of treatment of a subject undergoing such cosmetic or medical surgery, involving administration of a cross-linked product according to the invention to a subject in need thereof.

Preferred embodiments of these and other aspects of the present invention are also evident from the following disclosure, including the examples and the appended claims.

BRIEF DESCRIPTION OF THE DRAWINGS

FIG. 2 shows hydrolytic kinetic resolution of BDDE.

FIG. 3 shows derivatisation of enantiomerically enriched BDDE for enantiopurity measurement.

FIG. 8 shows enzyme-induced degradation of HA cross-linked with S,S-BDDE.

DETAILED DESCRIPTION OF THE INVENTION

Figure 1:
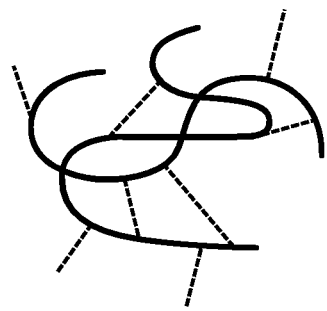
FIG. 1 schematically illustrates the structure of HA cross-linked with enantiopure BDDE and racemic BDDE, respectively.
Figure 1:
Figure 1:
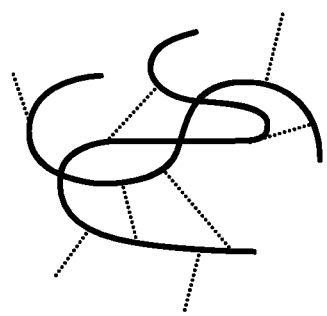
Figure 1:
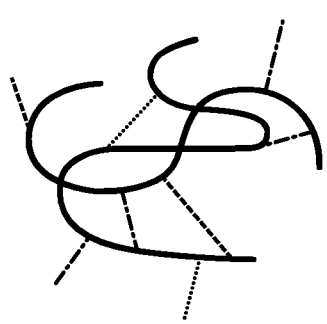

Unless otherwise provided, the terms "hyaluronic acid" and "HA" are used interchangeably and encompass all variants and combinations of variants of hyaluronic acid, or hyaluronan, of various chain lengths and charge states, as well as with various chemical modifications That is, the term also encompasses the various hyaluronate salts of HA, such as sodium hyaluronate (NaHA). Various modifications of the HA are also encompassed by the term, such as oxidation, e.g. oxidation of $CH_2OH$ groups to COOH; periodate oxidation of vicinal hydroxyl groups, optionally followed by reduction or imine formation etc; reduction, e.g. reduction of COOH to $CH_2OH$; sulphation; deamidation, optionally followed by deamination or amide formation with new acids; esterification; substitutions with various compounds, e.g. using a cross-linking agent or a carbodiimide; including coupling of different molecules, such as proteins, peptides and active drug components, to HA; and deacetylation. It is well known to the skilled person that the various forms of HA have different chemical properties that have to be taken into account during chemical modification and analysis. For instance, if it is desired to obtain a solution of HA having a certain pH, the acidity of the material to be dissolved, the acidity of the dissolving liquid and any buffering capacity will all affect the resulting pH of the solution.

It is preferred that the HA substrate is a HA or hyaluronate salt without chemical modifications.

The HA can be obtained from various sources of animal and non-animal origin. Sources of non-animal origin include yeast and preferably bacteria. The molecular weight of a single HA molecule is typically in the range of 0.8-3 MDa, but other ranges of molecular weights are possible, e.g. 0.1-10 MDa.

The product that is manufactured by the method is preferably a cross-linked HA. The method provides ether or ester cross-links, preferably ether cross-links, between the HA chains, which creates a continuous shaped network of HA molecules which is held together by the covalent cross-links, physical entangling of the HA chains and various interactions, such as hydrogen bonding, van der Waals forces and electrostatic interactions. The cross-linked HA product according to the invention is a gel, or a hydrogel. That is, it can be regarded as a water-insoluble, but substantially dilute, cross-linked system of HA molecules when subjected to a liquid, typically an aqueous liquid.

The resulting cross-linked HA product is preferably biocompatible. This implies that no, or only very mild, immune response occurs in the treated individual.

To the best of our knowledge, the BDDE used in production of cross-linked HA hydrogels has always been racemic BDDE. The two epoxides on BDDE can be alternatively of S or R configuration. The commercially available BDDE is a racemic mixture with the following composition: 25% of (R,R) stereoisomer, 25% of (S,S) stereoisomer and 50% of (S,R) or (R,S) stereoisomer which is a meso form.
Composition of Commercial Racemic BDDE:

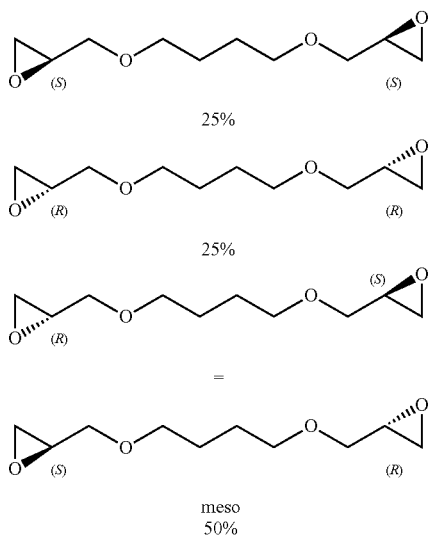

Using this commercially available racemic BDDE in a HA crosslinking reaction induces the incorporation of these three stereoisomers into the macromolecular network by ether or ester bonds, preferably ether bonds. Using a mixture of stereoisomers of BDDE in the cross-linking of HA induces a randomly oriented network with ether or ester bonds, preferably ether bonds. Using enantiopure or enantioenriched BDDE in the cross-linking of HA results in a more defined network of ether or ester bonds, preferably ether bonds, which alter and may improve the properties of the cross-linked HA hydrogel. See FIG. 1.

Enantiopure or enantioenriched BDDE (e.g. predominantly (S,S) configuration or (R,R) configuration) can be synthesized by several methods known by a man of the art, for example: stereoselective hydrolysis of racemic BDDE or alkylation of dibromobutane by enantiopure glycidol or alkylation of butanediol by enantiopure epichlorohydrine or stereoselective epoxidation of butanediol diallyl ether, etc. Thus, according to one aspect, the present invention provides a process for preparing an enantiopure BDDE or and enantioenriched mixture of BDDE stereisomers.

The present invention provides according to one aspect a compound selected from the following enantiomers of BDDE:

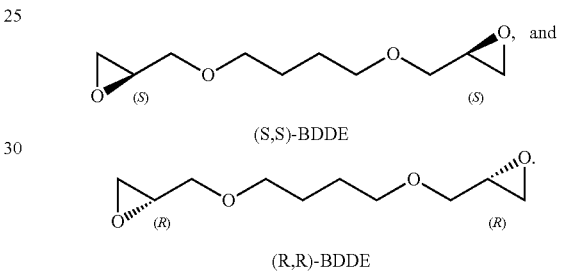

The separation of enantiomers of BDDE allows for cross-linking reactions with new proportions of the BDDE stereoisomers compared to the commercial racemic mixture. This allows for manufacture of new cross-linking products, e.g. with a more defined network of ether or ester bonds, preferably ether bonds, which alter and may improve the properties of the cross-linked product. A preferred example relates to cross-linking of HA. The enantioenriched or enantiopure BDDE may also be a cross linking agent for a compound selected from the group consisting of amylose, xylan, hydroxyethyl cellulose and dextran; polyethylenimine; glycosaminoglycans, including hyaluronic acid; and amine or hydroxyl containing bis-epoxy supports. A preferred group of compounds are glycosaminoglycans, including heparin, heparan sulfate, chondroitin, chondroitin sulfate, dermatan, dermatan sulfate, keratan, keratan sulfate, and hyaluronic acid, as well as derivatives thereof.

In some preferred embodiments, the enantiomer of BDDE is (S,S)-BDDE. In other preferred embodiments, the enantiomer of BDDE is (R,R)-BDDE.

According to another aspect, the present invention provides an enantioenriched mixture of BDDE stereisomers, wherein one of the following enantiomers of BDDE is present in a percentage share of at least 50%:

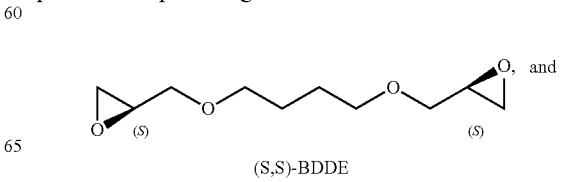

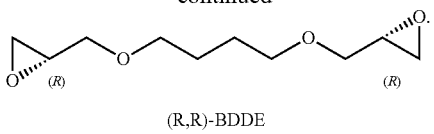

(R,R)-BDDE

In certain embodiments, the percentage share of the enantioenriched enantiomer is at least 70%, such as at least 80%, such as at least 95%.

According to a related aspect, the present invention provides enantiopure BDDE, consisting of one of the following enantiomers of BDDE:

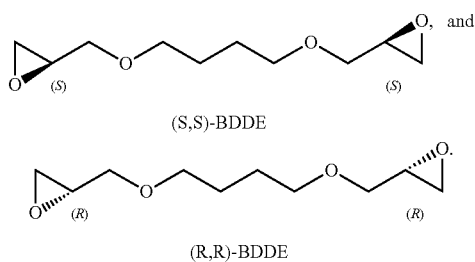

(S,S)-BDDE (R,R)-BDDE

In certain embodiments of these aspects, the enantiomer of BDDE is (S,S)-BDDE. In other embodiments of these aspects, the enantiomer of BDDE is (R,R)-BDDE.

According to one aspect, the present invention provides use of an enantioenriched mixture of BDDE stereisomers according to the invention or an enantiopure BDDE according to the invention as a cross-linking agent. The enantioenriched or enantiopure BDDE may e.g. be a cross linking agent for a compound selected from the group consisting of amylose, xylan, hydroxyethyl cellulose and dextran; polyethylenimine; glycosaminoglycans, including hyaluronic acid; and amine or hydroxyl containing bis-epoxy supports. A preferred group of compounds are glycosaminoglycans, including heparin, heparan sulfate, chondroitin, chondroitin sulfate, dermatan, dermatan sulfate, keratan, keratan sulfate, and hyaluronic acid, as well as derivatives thereof. In a preferred embodiment, the use of the enantioenriched mixture of BDDE stereisomers according to the invention or the enantiopure BDDE according to the invention is as a cross-linking agent for HA.

According to a related aspect, the present invention provides a process for preparing a cross-linked product according to the invention, comprising the step of cross-linking a compound (substrate) selected from the group consisting of amylose, xylan, hydroxyethyl cellulose and dextran; polyethylenimine; glycosaminoglycans, including hyaluronic acid; and amine or hydroxyl containing bis-epoxy supports, using an enantioenriched mixture of BDDE stereisomers according to the invention or an enantiopure BDDE according to the invention as cross-linking agent. A preferred group of compounds are glycosaminoglycans, including heparin, heparan sulfate, chondroitin, chondroitin sulfate, dermatan, dermatan sulfate, keratan, keratan sulfate, and hyaluronic acid, as well as derivatives thereof.

According to a related aspect, the present invention provides a process for preparing a cross-linked hyaluronic acid product according to the invention, comprising the step of cross-linking hyaluronic acid using an enantioenriched mixture of BDDE stereisomers according to the invention or an enantiopure BDDE according to the invention as cross-linking agent.

Typically, the substrate, e.g. HA, is dissolved in an aqueous solution containing hydroxide. Under the basic conditions (pH≤9) employed in the cross-linking-step, BDDE provides ether cross-links between the substrate molecules, such as the HA chains. Alternatively, acidic conditions (pH≤9) may be employed in the cross-linking step to provide ester bonds. If a combination of ether and ester bonds are desirable, the cross-linking may be performed under neutral conditions (pH 7-9), or stepwise using first basic conditions (pH≤9), followed by acidic conditions (pH 9), optionally including addition of further cross-linking agent. The amount of cross-linking agent used is not critical.

The cross-linking agent can be added to the aqueous solution prior to, at the same time as, or after addition of the substrate, e.g. HA. The cross-linking agent and/or the substrate, e.g. HA, can also be added to the aqueous solution in portions in any suitable order.

The reactants are the allowed to cross-link and form a cross-linked product, such as an HA gel, by subjecting the aqueous solution to cross-linking conditions, which typically involves a desirable time and temperature. In general terms, this cross-linking step can be made using any suitable concentrations of substrate, e.g. HA, and of cross-linking agent, and the time and temperature can vary. The dissolved substrate, e.g. HA, is allowed to react with the cross-linking agent for a suitable time to obtain a cross-linked product, e.g. an HA gel.

The cross-linking step is typically carried out at a temperature of 10-75° C., but it is preferred that the step is carried out at room temperature, e.g. 20-25° C. Preferred temperature ranges are 10-50° C., such as 18-40° C.

Due to the cross-linking, the resulting HA product is a continuous network of interconnected and entangled HA chains which absorbs liquid (swells) and forms a gel. That is, it can be regarded as a water-insoluble, but substantially dilute cross-linked system of HA molecules when subjected to a liquid, typically an aqueous liquid. The gel is mostly liquid by weight and can e.g. contain 90-99.9% water, but it behaves like a solid due to a three-dimensional cross-linked HA network within the liquid. Due to its significant liquid content, the shaped gel is structurally flexible and similar to natural tissue, which makes it very useful as a scaffold in tissue engineering and for tissue augmentation.

The swelling of the resulting HA gel can be allowed to proceed until the gel is fully swollen and no further liquid can be absorbed, or it can be interrupted at an earlier stage to obtain a partially swollen gel. A partially swollen gel can be useful as an intermediate for further processing of the gel, for instance further mechanical production of gel structures of a desired size and shape can be performed. It may also be convenient to use a partially swollen shaped gel product during implantation thereof at a desired site to facilitate administration and minimize patient discomfort and to enhance the lifting capacity by use of the remaining swelling capacity.

The resulting hydrogels of HA or other substrates using enantiopure BDDE will be composed of only one stereoisomer of BDDE. The macromolecular network obtained with enantiopure BDDE is different from the one obtained with racemic BDDE and has never been synthesized even as a mixture when racemic BDDE was used, i.e., the HA hydrogels formed using enantiopure BDDE are not a subset of the HA hydrogels formed using racemic BDDE. See FIG. 1 schematically illustrating the difference between HA cross-linked with enantiopure BDDE and HA cross-linked with racemic BDDE.

Similarly, the resulting hydrogels of HA or other substrates using enantioenriched BDDE will be composed of a combination of BDDE stereoisomer which is different from that resulting from the use of commercial racemic BDDE. The macromolecular network obtained with enantioenriched BDDE is different from the one obtained with racemic BDDE.

Thus, according to one aspect, the present invention provides a cross-linked product, wherein a compound selected from the group consisting of amylose, xylan, hydroxyethyl cellulose and dextran; polyethylenimine; glycosaminoglycans, including hyaluronic acid; and amine or hydroxyl containing bis-epoxy supports, is cross-linked with an enantioenriched mixture of BDDE stereisomers according to the invention, or with an enantiopure BDDE according to the invention. A preferred group of compounds are glycosaminoglycans, including heparin, heparan sulfate, chondroitin, chondroitin sulfate, dermatan, dermatan sulfate, keratan, keratan sulfate, and hyaluronic acid, as well as derivatives thereof.

In particular, the present invention provides a cross-linked hyaluronic acid product, wherein the hyaluronic acid is cross-linked with an enantioenriched mixture of BDDE stereisomers according to the invention, or with an enantiopure BDDE according to the invention.

According to a related aspect, the present invention provides a cross-linked product, e.g. an HA gel, obtainable, or even obtained, by the process according to the invention. The product can advantageously be further characterized by one or more of the following features.

In a preferred embodiment, the substrate, e.g. HA, is cross-linked via ether bonds to the BDDE. In another preferred embodiment, the substrate, e.g. HA, is cross-linked via ester bonds to the BDDE. In one preferred embodiment, the substrate, e.g. HA, is cross-linked via a mixture of ether and ester bonds to the BDDE. In a preferred embodiment, the cross-linked product, e.g. cross-linked HA, is a gel.

Interestingly, the resistance profile towards enzyme degradation of enantiopure or enantioenriched BDDE cross-linked HA is different compared to racemic BDDE cross-linked HA. Results indicate that one of the stereochemical configurations of BDDE (e.g. (S,S) configuration or (R,R) configuration) is more resistant towards enzyme degradation by chondroitinase. Without desiring to be bound to any particular scientific theory, this could be explained by the mode of action of an enzyme on a polymer; the polymer has to fit in a three-dimensional pocket of the enzyme in order to obtain the degradation. A HA hydrogel obtained by cross-linking with BDDE will be more difficult to fit in the enzyme pocket closer to a substitution position. Furthermore, this could also depend on the stereochemistry of the BDDE, i.e. the (S,S) configuration and (R,R) configuration give HA hydrogels with different conformations, and hence different ability to fit in the three-dimensional pocket of an enzyme. This may be reflected in different resistance to enzyme degradation for several HA degrading enzymes such as hylauronidase hydrolases and lyases.

The hyaluronic acid hydrogel obtained have preferably a degree of modification (namely the ratio of moles of linked BDDE to moles of HA-disaccharides) comprised between 0.01% and 20%, more preferably between 0.1% and 10%.

The enantiomeric excess of enantioenriched BDDE is comprised between 50% and 100%, more preferably between 70% and 100%, such as between 80% and 100%.

The HA hydrogel obtained is characterized by the swelling, i.e. the ability to absorb water, and the viscoelastic properties. Swelling is expressed as the amount of water in gram that one gram cross-linked dry HA polymer can absorb. The viscoelastic properties are measured by rheometry, and are expressed as the storage modulus (G') and the loss modulus (G").

It is preferable that the cross-linked HA gel products according to the invention are viscoelastic. This implies that the gel products exhibit a combination of viscous and elastic properties. As is well known by the skilled person, the viscoelastic properties can be determined with a rheometer. In oscillating mode, the elastic modulus (G') and the viscous modulus (G") can be determined at a frequency of e.g. 0.1 or 1 Hz. For certain viscoelastic gel products according to the invention, it is preferred that the following relationship is satisfied:

$$0.1 \leq \frac{G'}{(G'' + G')} \leq 0.98, \text{ preferably } 0.5 \leq \frac{G'}{(G'' + G')} \leq 0.98.$$

The chemical composition of the HA hydrogel is obtained by proton NMR spectroscopy after degradation of the HA polysaccharide strands by hylauronidase or equivalent to obtain sharp lines in the spectrum enabling proper quantification.

The gel content of the resulting cross-linked HA product describes in % the proportion of the total HA that is bound in gel form, i.e. the proportion that cannot be removed by filtration or dialysis. In a preferred embodiment, the gel content of the product is 80% or higher, such as 90% or higher. It is preferred that the gel content is within the limits set out above also for the corresponding cross-linked HA gel product following autoclaving by heat.

The product according to the invention can be manufactured in various shapes, such as a particle, a fibre, a string, a strand, a net, a film, a disc or a bead. It is preferred that the shape has an extension of less than 5 mm, preferably less than 1 mm, and larger than 0.5 mm or even larger than 0.8 mm when the HA substrate is in swollen form in physiological saline. A preferred shape is particles or beads having a size of 0.1-5 mm, such as 0.5-1 mm, when fully swollen in physiological saline.

The desired shape and size can be achieved by subjecting the gel to mechanical disruption, such as mincing, mashing or passing the swollen or partly swollen gel through a filter or mesh with suitable pore size. The resulting gel particles or pieces are dispersed in a physiological salt solution, resulting in a gel dispersion or slurry with particles of desired size and shape. Depending on the shape, the size of a gel structure may be determined in any suitable way, such as by laser diffraction, microscopy, filtration, etc, and is decided by the longest distance between two ends of the particle. For spherical structures, the diameter equals the size for this purpose.

According to one embodiment of the invention, a cross-linked gel product, such as an HA gel, may be useful as a drug delivery device and be used in a method of drug delivery.

The cross-linked product, e.g. cross-linked HA, according to the invention is useful for hydrating and/or vitalizing the skin. For this purpose, the product may e.g. be injected into the skin or included in a cream which is applied to the skin.

The cross-linked product, e.g. cross-linked HA, according to the invention is useful in cosmetic or medical surgery. Non-limiting examples of cosmetic surgery are dermal filling, body contouring and facial contouring, in particular facial contouring. Non-limiting examples of medical surgery are dermal filling, body contouring, prevention of tissue adhesion, orthopaedic applications, incontinence treatment, treatment of vesicoureteral reflux (VUR), and formation of channels for draining purposes, e.g. in ophthalmology, and for keeping tissues apart.

According to one aspect, the present invention provides a method of treatment of a subject undergoing cosmetic or medical surgery, involving administration of a cross-linked product, e.g. cross-linked HA, according to the invention to a subject in need thereof. Non-limiting examples of medical surgery are dermal filling, body contouring, prevention of tissue adhesion, orthopaedic applications, e.g. hip and joint therapy, and formation of channels for draining purposes, e.g. in ophthalmology, and for keeping tissues apart.

In one preferred embodiment, the cross-linked product, e.g. cross-linked HA, is a dermal filler product.

According to one aspect, the present invention provides a method of treatment of skin aging signs wherein the cross-linked product, e.g. cross-linked HA, according to the invention is injected into the skin.

Useful gel structure size ranges and shapes depend on the intended application. For soft tissue augmentation, preferably subcutaneous administration, submuscular administration or supraperiostal administration, gel particles, pieces or fibres having a size, when subjected to a physiological salt solution, of more than 0.1 mm are useful. The term "soft tissue augmentation", as used herein, refers to any type of volume augmentation of soft tissues, including, but not limited to, facial contouring (e.g. more pronounced cheeks or chin), correction of concave deformities (e.g. post-traumatic, HIV associated lipoatrophy) and correction of deep age-related facial folds. Thus, soft tissue augmentation may be used solely for cosmetic purposes or for medical purposes, such as following trauma or degenerative disease. These two purposes are easily distinguished by the skilled person. The term "soft tissue", as used herein, refers to tissues that connect, support, or surround other structures and organs of the body. Soft tissue includes muscles, fibrous tissues and fat. Soft tissue augmentation may be performed in any mammal, including man. It is preferred that the method is performed in a human subject.

The terms "subepidermal administration" or "subcuticular administration", as used herein, refer to administration beneath the epidermis of the skin, including administration into the dermis, subcutis or deeper, such as submuscularly or into the periosteum where applicable (in the vicinity of bone tissue).

Administration of gel structures may be performed in any suitable way, such as via injection from standard cannulae and needles of appropriate sizes or surgical insertion, e.g. in the case of administration of a film. The administration is performed where the soft tissue augmentation is desired, such as the chin, cheeks or elsewhere in the face or body. It is preferred to utilize the gel and the gel structures in facial contouring.

An implant according to the invention may be an aqueous composition comprising the cross-linked HA product according to the invention, e.g. in the shape of ≥0.1 mm large HA gel structures, such as particles, beads, fibres or cut-out stripes, and optionally a buffering agent and/or a tonicity agent. The composition may typically contain a physiological salt buffer.

If desired, other substances, such as local anaesthetics (e.g. lidocaine hydrochloride), anti-inflammatory drugs, antibiotics and other suitable supportive medications, e.g. bone growth factors or cells, may be added after the cross-linked product, e.g. cross-linked HA, has been obtained.

The process according to the invention may also comprise one or more further steps.

Optionally, the manufacturing process involves a step of isolating the cross-linked product, e.g. cross-linked HA, e.g. by filtration, dialysis or precipitation to remove cross-linking agent which has not been incorporated into the cross-linked product.

Optionally, the manufacturing process involves a further step of sterilizing the cross-linked product, e.g. cross-linked HA, e.g. by autoclaving, radiation, heating etc., so as to obtain a sterile cross-linked product.

The cross-linked product, e.g. cross-linked HA, according to the invention, or an aqueous composition thereof, may be provided in a pre-filled syringe, i.e. a syringe that is prefilled with a sterilized, cross-linked product or a sterilized aqueous composition comprising the product. Optionally, the cross-linked product may be kept in precipitated form in a syringe, bag or other suitable container and be brought to its non-precipitated form prior to injection or in the body following injection thereof.

It is preferred that the swelled or partly swelled, cross-linked product, e.g. cross-linked HA, is autoclavable, since this is the most convenient way of sterilising the final product. This allows for preparation of a sterile, cross-linked product, e.g. cross-linked HA.

It goes without saying that the size of the gel structures, e.g. fibres, according to the invention is dependent upon how much the gel has been allowed to swell, and the ionic strength of the buffer, solution or carrier that is included in and/or surrounding the gel structures. Throughout this specification, given structure sizes assume physiological conditions, particularly isotonic conditions. It shall be noted that, while it is preferred that the gel structures contain and are dispersed in a physiological salt solution, it is contemplated that the gel structures according to the invention can temporarily be brought to different sizes by subjecting the gel structures to a solution of another tonicity, different pH or if the gel structures have not been allowed to swell to their maximum size.

As used herein, a physiological, or isotonic, solution is a solution having an osmolarity in the range of 200-400 mOsm/l, preferably 250-350 mOsm/l, more preferably approximately 300 mOsm/l.

The cross-linked HA gel product according to the invention is stable, but not permanent, under physiological conditions. According to an embodiment of the invention, at least 70%, preferably at least 90%, of the cross-linked HA gel product remains for at least two weeks in vivo, more preferably between two weeks and two years. The term "degraded" implies that less than 20%, preferably less than 10%, of the medium remains in the body.

Itemized Listing of Preferred Embodiments

1) Enantiopure or enantioenriched butanediol diglycidyl ether (BDDE).
2) Use of enantiopure or enantioenriched butanediol diglycidyl ether as a new crosslinking agent.

3) New hydrogel made of hyaluronic acid (HA) and enantiopure or enantioenriched BDDE.
4) Process to obtain enantipure or enantioenriched BDDE according to embodiment 1.
5) Process to obtain hydrogel according to embodiment 3.
6) Use of the hydrogel according to embodiment 3 as a dermal filler.
7) Method of treatment of skin aging signs wherein the hydrogel according to embodiment 3 is injected into the skin.

Without desiring to be limited thereto, the present invention will in the following be illustrated by way of examples.

EXAMPLES

Example 1—Enantioenriched R,R-BDDE

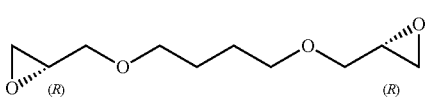

Hydrolytic kinetic resolution was used for the preparation of enantiomerically enriched BDDE from racemic BDDE (FIG. 2). Enantiomeric excess (ee) was determined using a chiral HPLC column after derivatization of enantiomerically enriched BDDE (FIG. 3), while the absolute configuration was obtained using VCD associated with density functional theory (DFT) calculations.

(A) Enantioenriched R,R-BDDE

To a stirred solution of (1S,2S)-(+1,2-cyclohexanediamino-N,N'-bis(3,5-di-t-butylsalicylidene)cobalt(II) (0.60 g; 0.99 mmol; 0.01 eq.) in 10 ml dichloromethane (DCM) at 23° C. acetic acid was added (566 µl; 9.89 mmol; 0.10 eq.) and the reaction mixture stirred at 23° C. under air for 30 min. Once the color changed from red to dark brown (Co(II) to Co(III) oxidation) the reaction mixture was evaporated to dryness under vacuum. The catalyst was then dissolved in THF (20.0 ml) and racemic BDDE (18.2 ml; 98.9 mmol; 1.00 eq.) was added. The mixture was cooled down to 0° C. and water (1.43 ml; 79.1 mmol; 0.80 eq.) was added. The reaction mixture was allowed to warm up to 23° C. and stirred at this temperature for 24 h. After this time, the reaction mixture was evaporated to dryness. The dark red oil was purified two times by column chromatography on silica gel eluting with DCM and then with DCM/diisopropyl ether 85/15 to yield enantiomerically enriched (2'R,2"R)-BDDE (3.60 g; 18% yield) as a pale brown oil.

$^1$H NMR (400 MHz, DMSO-d$_6$): δ 3.67 (dd, J=11.6, 2.8 Hz, 2H), 3.49-3.38 (m, 4H), 3.23 (dd, J=11.5, 6.3 Hz, 2H), 3.09 (ddt, J=6.9, 4.3, 2.8 Hz, 2H), 2.72 (dd, J=5.2, 4.2 Hz, 2H), 2.54 (dd, J=5.2, 2.7 Hz, 2H), 1.58-1.51 (m, 4H).

(B) Derivatization of Enantiomerically Enriched R,R-BDDE for Enantiopurity Measurement To a stirred solution of enantiomerically enriched (2'R, 2"R)-BDDE (300 mg; 1.48 mmol; 1.00 eq.) in methanol (3.00 ml) at 0° C. was added 2-naphthalenethiol (0.48 g; 2.97 mmol; 2.00 eq.) followed by triethylamine (411 µl; 2.97 mmol; 2.00 eq.). The reaction mixture was stirred at 0° C. for 2 h and then allowed to warm up to 23° C. and stirred at this temperature for 18 h. The reaction mixture was filtered and the filtrate partitioned between DCM (50 mL) and water (50 mL). Phases were separated and the organic layer was washed with 1 M aqueous HCl (50 mL), dried over MgSO$_4$ and evaporated to dryness to yield the desired product (700 mg; 90% yield) as a colorless oil.

$^1$H NMR (400 MHz, DMSO-d$_6$): δ 7.88-7.75 (m, 8H), 7.53-7.38 (m, 6H), 5.18 (d, J=5.3 Hz, 2H), 3.80 (h, J=5.4 Hz, 2H), 3.46-3.32 (m, 8H), 3.21 (dd, J=13.3, 5.2 Hz, 2H), 3.05 (dd, J=13.3, 6.6 Hz, 2H), 1.57-1.40 (m, 4H). MS (m/z, ES$^+$): 545.2 ([M+Na]$^+$)

HPLC with a chiral column was recorded on an Agilent 1100 Series system using the following parameters: Column: Chiralpak ID 5 µm, 250×4.6 mm; Flow rate=1.0 mL/min; 30.0 min runs; solvent system: heptane 65%, iPrOH 35%; isocratic flow. Chiral HPLC showed the following ratio: enantiomer 1 ($t_R$=19.9 min): 5%; meso isomer ($t_R$=22.8 min): 7%; enantiomer 2 ($t_R$=26.2 min): 86%.

(C) 2.7 Determination of Absolute Configuration

A FTIR spectrometer (Vertex 70, Bruker) equipped with a vibrational circular dichroism (VCD) module (PMA 50, Bruker) for VCD measurements was used.

Using VCD associated with density functional theory (DFT) calculations, the absolute configuration of this enantiomerically enriched BDDE was established to be (2'R,2"R), i.e. (R,R)-BDDE. The DFT calculations were carried out at 298 K in gas phase with Gaussian 09 software.

Example 2—Enantioenriched S,S-BDDE

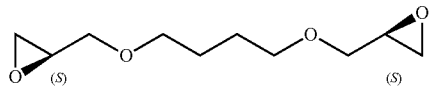

To a stirred solution of (1R,2R)-(+1,2-cyclohexanediamino-N,N'-bis(3,5-di-t-butylsalicylidene)cobalt(II) (4.48 g; 7.42 mmol; 0.01 eq.) in dichloromethane (75.00 ml) was added acetic acid (4.24 ml; 74.17 mmol; 0.10 eq.), and the reaction mixture was stirred at 23° C. under air for 30 min. Once the color changed from red to dark brown the reaction mixture was evaporated to dryness. The catalyst was dissolved in 1,4-butanediol diglycidyl ether (136.36 ml; 741.66 mmol; 1.00 eq.) and then tetrahydrofurane (150.00 ml) was added. The reaction mixture was cooled down to 0° C., and then water (8.02 ml; 444.99 mmol; 0.60 eq.) was added and the reaction mixture was allowed to warm up to 23° C., stirred at this temperature for 18 h and evaporated to dryness.

The resulting oil was purified by flash column chromatography over spherical silica (DCM/DIE 80/20) to yield a brown liquid (21.60 g; 14.40%). 10 g of this batch was purified by distillation under reduced pressure (P=0.3 mbar, temperature: 125° C., (4.20 g; 2.80%)) and was obtained as a colorless oil.

$^1$H NMR (400 MHz, DMSO-d$_6$): δ 3.67 (dd, J=11.6, 2.8 Hz, 2H), 3.49-3.38 (m, 4H), 3.23 (dd, J=11.5, 6.3 Hz, 2H), 3.09 (ddt, J=6.9, 4.3, 2.8 Hz, 2H), 2.72 (dd, J=5.2, 4.2 Hz, 2H), 2.54 (dd, J=5.2, 2.7 Hz, 2H), 1.58-1.51 (m, 4H).

This fraction showed 75% of the S,S-enantiomer of BDDE with 22% of the meso compound and 2% of the R,R-enantiomer of BDDE according to the derivatization protocol of Example 1B.

Example 3—Cross-Linking HA Using Enantioenriched BDDE as Cross-Linking Agent

HA (MW 1 MDa), 0.25 M NaOH and BDDE (R,R-enantioenriched from Example 1, S,S-enantioenriched from Example 2, or racemic) was mixed in a 50 mL Falcon tube. The cross-linking and the treatment of the resulting cross-linked HA were performed according to the general procedure described in Examples 1 and 2 of International patent publication WO 97/04012. HA was allowed to react with BDDE under alkaline conditions to prepare an ether cross-linked HA product, and the HA concentration was adjusted to 20 mg/ml after neutralization.

Example 4—Enzymatic Degradation of HA Cross-Linked with Enantioenriched R,R-BDDE HA hydrogels formed by reaction with R,R-BDDE and racemic BDDE were degraded using chondroitinase ABC. The fragments obtained from enzymatic digestion with chondroitinase ABC are unsaturated HA oligosaccharides which are abbreviated $\Delta HA_x$ where x refers to the length of the oligosaccharide. The fragments with mono-linked BDPE which are investigated in this work are abbreviated as $\Delta HA_x$-B. The monosaccharide residues within the chain are named $\Delta GlcA$ (unsaturated glucuronic acid), $GlcA_y$ (glucuronic acid), and $GlcNAc_y$ (N-acetyl glucosamine) where "y" indicates the position of the residue starting from the reducing end. The substitution positions are referred to as the monosaccharide residue together with the suffix —OHZ where "Z" is the position on the ring which is substituted.

The product mixture obtained after the enzymatic degradation was separated by anion exchange chromatography. The fractions corresponding to the monosubstituted di-, tetra- and hexasaccharides were collected for further analysis of the position of substitution by BDPE.

The hydrogels (1 g in 100 ml 1 mM sodium phosphate buffer pH 7.0) obtained in Example 3 by reaction with R,R-BDDE and racemic BDDE were treated with chondroitinase ABC (10 UN, Sigma Aldrich) in a sealed flask at 37° C. for 90 h.

The degradation was followed by analyzing the sample on a Superdex Peptide 10/300 GL column (GE Healthcare, Uppsala, Sweden) using analytical HPLC with a diode-array detector (LC10vp LC system, Shimadzu). The degradation was considered complete when the viscosity of the sample was low, no remaining gel particles were observed and the sample contained mostly low-molecular weight oligosaccharides as demonstrated by HPLC-MS analysis.

The enzyme digest was separated using preparative HPLC (AKTA purifier with UV-detector UV-900, pump P-900 and sample pump P-960, GE Healthcare, Uppsala, Sweden) in two steps. The first separation was performed by injecting 5 ml of the enzyme digest (sample pump, 5 ml/min) on to an in-house-packed QSepharose High Performance 16/170 column (GE Healthcare, Uppsala, Sweden) using a gradient of 1 mM sodium phosphate buffer pH 7.0 and 1 mM sodium phosphate buffer pH 7.0 with 200 mM sodium chloride (0-40% 43 min, 40% 6.5 min, 100% 9.5 min) at 5 ml/min. UV detection (232 nm) was used to monitor the separation, and fractions were collected automatically according to predetermined limits of the UV-signal. The content of the collected fractions were analysed with the Superdex Peptide 10/300 GL on the analytical HPLC. Fractions containing equal oligosaccharides were pooled and lyophilized.

The obtained powder from the fractions containing $\Delta HA_2$-B, $\Delta HA_4$-B, $\Delta HA_6$-B were dissolved in 10 ml of 100 mM ammonium acetate pH 7.8 and were then further purified from salt and other impurities on the AKTA purifier by injecting 1 ml with a sample loop on a self-packed Superdex Peptide Prep Grade 16/750 column (GE Healthcare, Uppsala, Sweden). Isocratic elution with 100 mM ammonium acetate pH 7.8 at 1.0 ml/min was used. UV detection (232 nm) was used to monitor the separation and fractions were collected automatically based on the UV-signal. The pure fractions containing $\Delta HA_2$-B, $\Delta HA_4$-B, $\Delta HA_6$-B were analysed with Superdex Peptide 10/300 GL on the analytical HPLC and then lyophilized. The fractions containing HA oligosaccharides at both ends of 1,4-butanediol di-(propan-2,3-diolyl)ether (BDPE) were also collected but not analyzed further.

Figure 4:
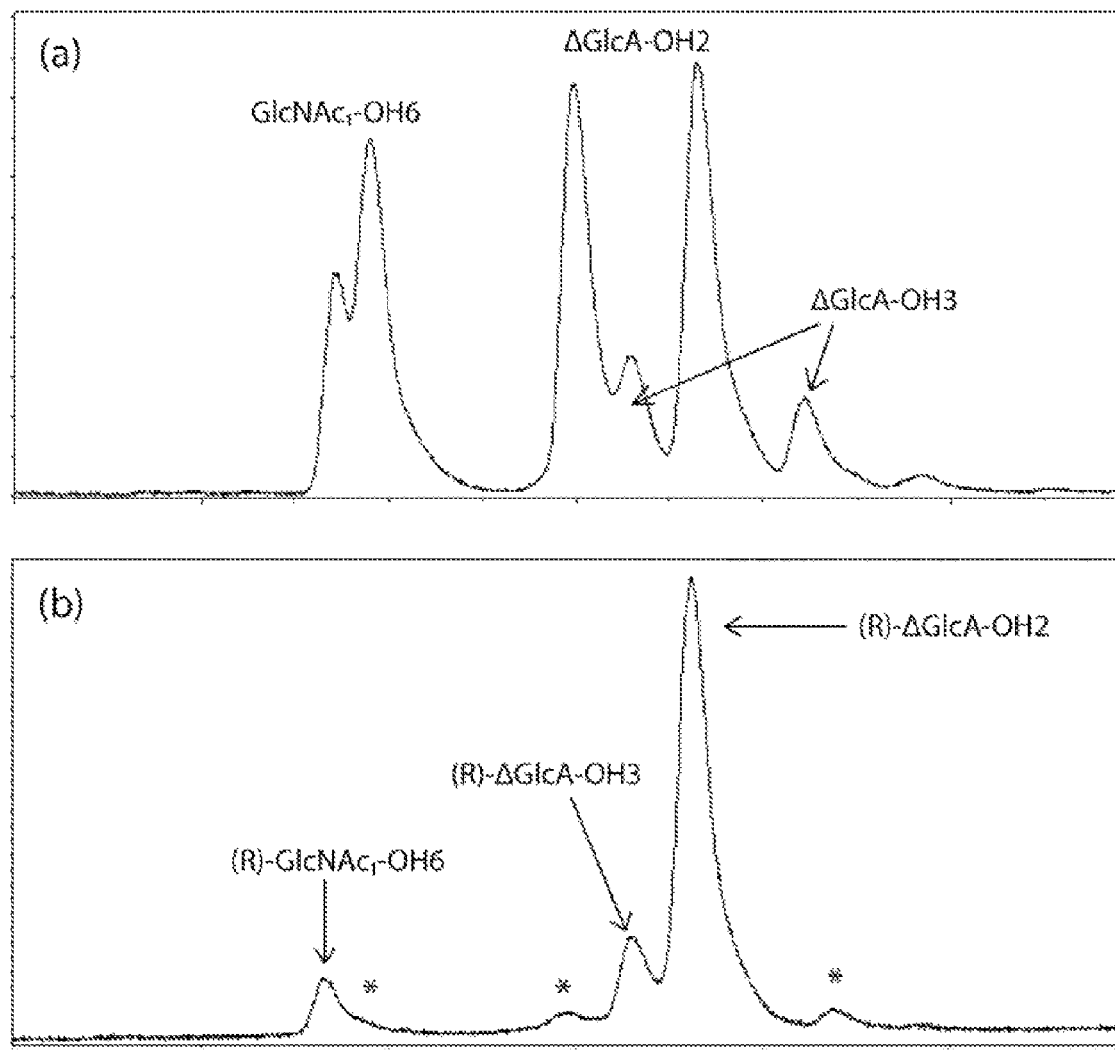
FIG. 4 shows LC-UV chromatograms of fractions of cross-linked HA following enzymatic cleavage.

In FIG. 4, panel (a) is a LC-UV chromatogram of fraction $\Delta HA_2$-B obtained from the HA gel prepared with racemic BDDE and after reduction by $NaBH_4$ in $NH_4OH$ showing the six resulting diastereoisomers. Panel (b) is a LC-UV chromatogram of $\Delta HA_2$-B fraction obtained from the HA gel prepared with (2'R,2"R) enantiomerically enriched BDDE, i.e. (R,R)-BDDE, and after reduction by $NaBH_4$. The three peaks marked with an asterisk (*) in FIG. 4b have decreased considerably in size compared to the corresponding peaks in FIG. 4a, hence showing which of the pairwise peaks in FIG. 4a that correspond to the (2'R,2"R) isomer of BDDE. The LC-UV analysis of the $\Delta HA_2$-B fraction obtained from the HA gel prepared with racemic BDDE showed that the amount of $\Delta HA_2$-B with GlcNAc-OH6 substitution by the (2'R,2"R) isomer of BDDE is lower than for substitution by the (2'S,2"S) isomer (FIG. 4a). This indicates that the enzymatic degradation has proceeded slower, or to a lesser extent, with the HA gel prepared with (2'R,2"R) enantiomerically enriched BDDE than with the HA gel prepared with racemic BDDE.

Example 5—Degradation of HA Cross-Linked with Enantioenriched R,R-BDDE

Cross-linked HA gel formed by reaction with enantioenriched R,R-BDDE was subjected to degradation with heat, peroxyl radicals and hyaluronidase enzyme.

(A) Heat Degradation

Samples of approximately 0.25 g HA hydrogel formed by reaction with enantioenriched R,R-BDDE were weighed into ten 15 mL glass vials and to each vial 9.75 g of 0.7% sodium chloride in 8 mM phosphate buffer pH 7 was added. The vials were closed and the contents were mixed for at least 2 hours. The vials were immersed into a 90° C. water bath for 0, 16, 24, 32 and 48 hours, respectively. After immediate cooling in cold water, the contents of the vials were mixed over night. The supernatants were filtered through a 0.2 μm filter and analyzed for HA content using the carbazole method. The heat degradation of the HA gel was evaluated over time with the residual gel (%) at each time point with 100% residual gel at time zero.

Figure 5:
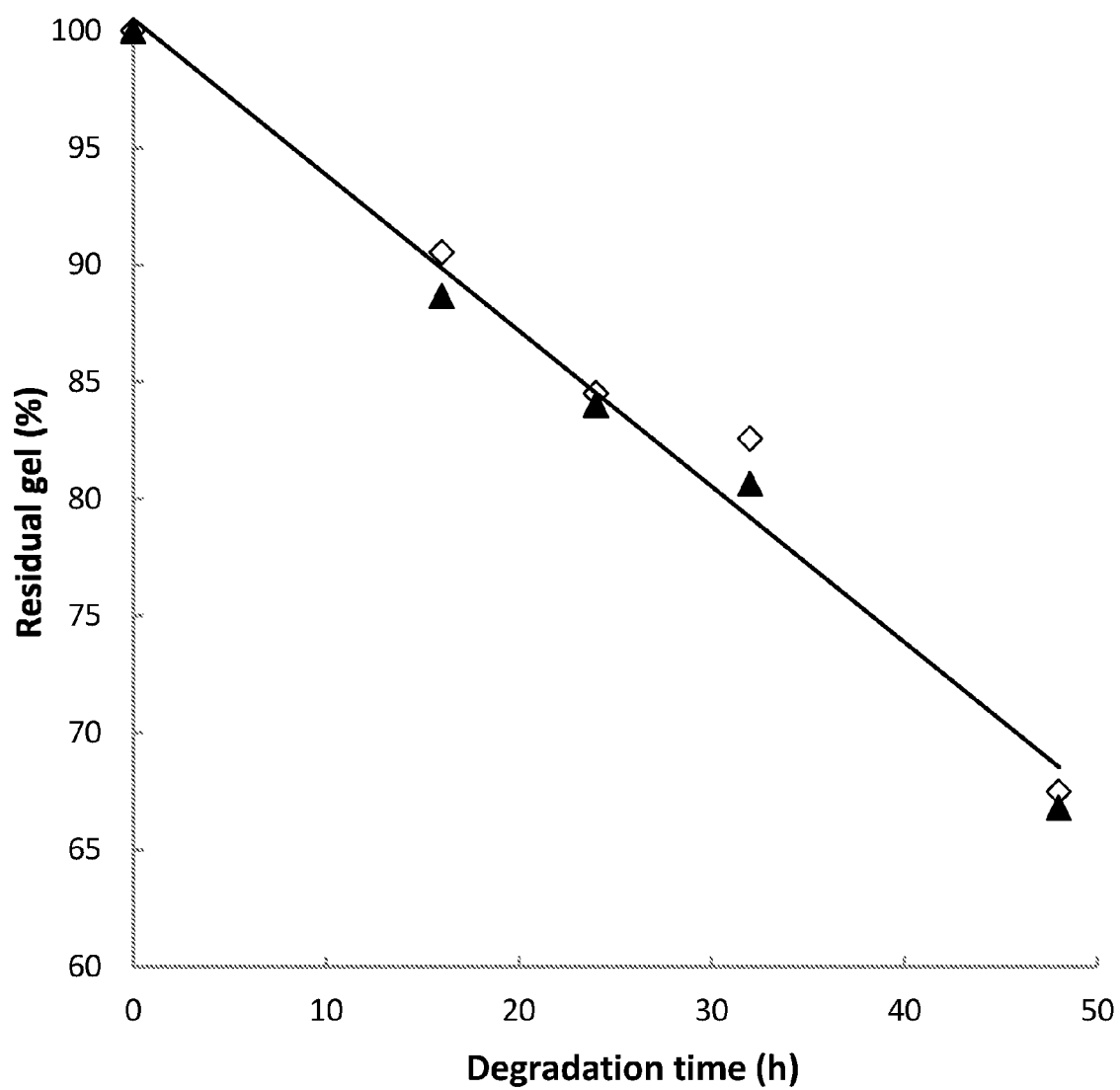
FIG. 5 shows heat-induced degradation of HA cross-linked with R,R-BDDE.

The results from duplicate hydrogel batches (filled triangles; empty diamonds) are shown in FIG. 5.

(B) Radical Degradation

Samples of approximately 0.25 g HA hydrogel formed by reaction with enantioenriched R,R-BDDE were weighed into two 15 mL vials and to each vial 8.75 g of 0.9% sodium chloride in 20 mM phosphate buffer pH 7.5 was added. The vials were closed and the contents were mixed over night. Immediately before starting the radical degradation 1 mL of 100 mM 2,2'-azobis-2-methylpropionamide hydrochloride (AAPH) in buffer was added to each vial. The vials were immersed into a 37° C. water bath and 0.5 mL aliquots of the supernatant were collected from each vial at 0, 1.5, 2.5 and 3.5 hours, respectively. The collected aliquots were filtrated though 0.2 μm filter immediately. The filtrates were analyzed for HA content, and the radical degradation of the HA gel was evaluated over time as the residual gel (%) at each time point with 100% residual gel at time zero.

Figure 6:
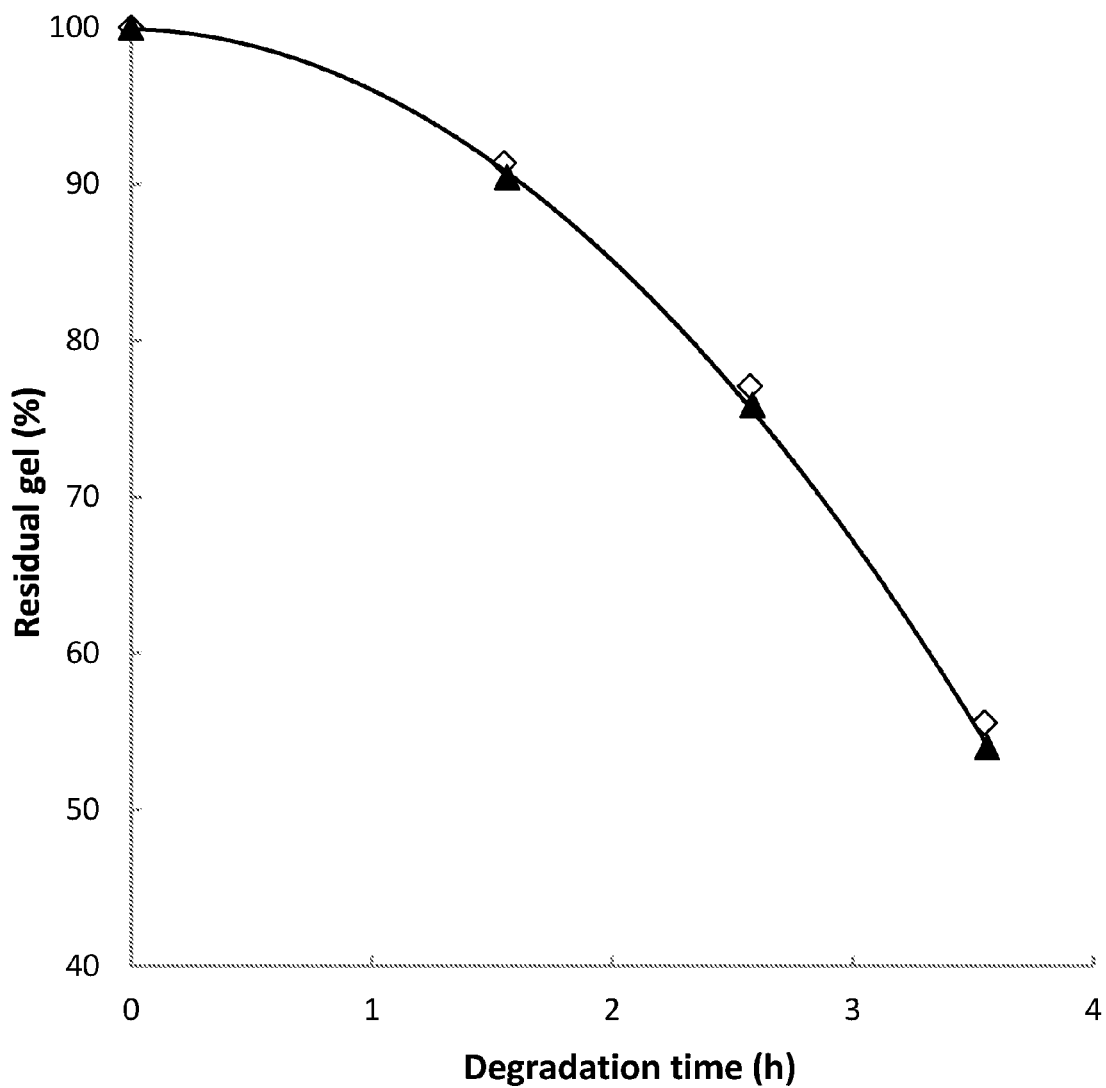
FIG. 6 shows radical-induced degradation of HA cross-linked with R,R-BDDE.

The results from duplicate hydrogel batches (filled triangles; empty diamonds) are plotted in FIG. 6.

(C) Hyaluronidase Degradation

Samples of approximately 0.5 g HA hydrogel formed by reaction with enantioenriched R,R-BDDE were weighed into eight 4 mL glass vials. The test tubes were centrifuged at 2500 g during 3 minutes to collect all gel in the bottom of the tubes. Five hundred microliters of freshly prepared 30 U/mL hyluronidase solution (sheep testes, Type V) was added to all samples except the time zero samples to which 500 μL of 0.9% sodium chloride solution was added instead. All samples were shaken gently before incubation at 37° C. in a water bath. The time zero and 1 hour samples were taken at one hour. More samples were taken at approximately 2.5 and 4 hours, respectively. Duplicate samples were taken at each time point.

After sampling, the content of the vials were immediately poured into separate pre-weighed 50 mL Falcon tubes. The vials were washed at least three times with 0.9% sodium chloride solution and the washing solutions were poured into the same Falcon tube. Thereafter, 0.9% sodium chloride solution was added to a final volume of about 30 mL in each tube. The Falcon tubes were weighed, shaken vigorously and centrifuged at 2500 g for 3 minutes. Approx. 1.5 mL supernatant was drawn from the samples and filtered through a 0.2 μm syringe filter into LC vials. The filtrates were analyzed for HA content, and the hyaluronidase degradation of the HA gel was evaluated over time as the residual gel (%) at each time point with 100% residual gel at time zero.

Figure 7:
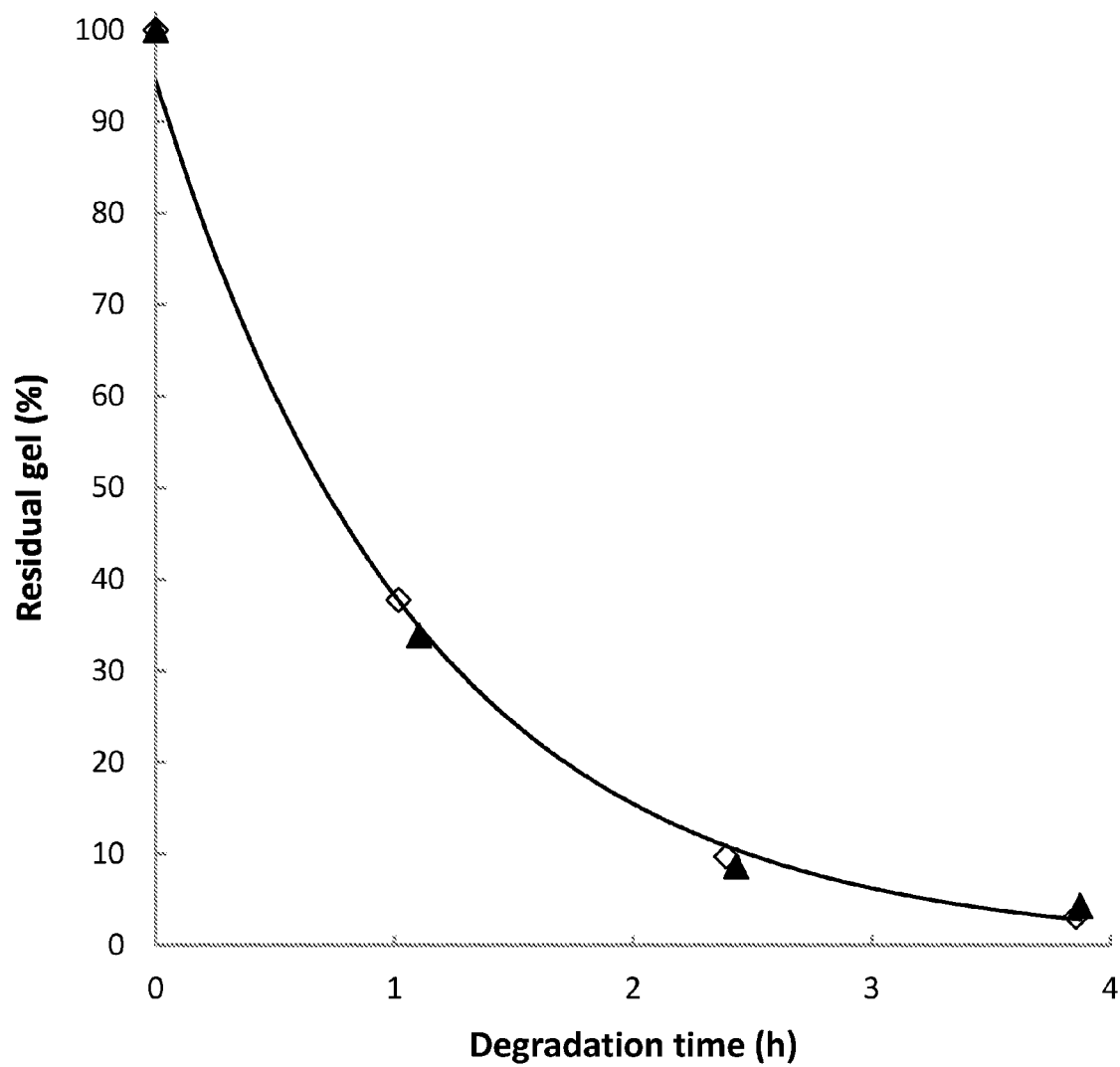
FIG. 7 shows enzyme-induced degradation of HA cross-linked with R,R-BDDE.

The results from duplicate hydrogel batches (filled triangles; empty diamonds) are plotted in FIG. 7.

Example 6—Enzymatic Degradation of HA Cross-Linked with Enantioenriched S,S-BDDE Samples of approximately 0.5 g HA hydrogel formed by reaction with enantioenriched S,S-BDDE were subjected to enxymatic degradation with hyluronidase (sheep testes, Type V) as set out in Example 5C. The results are shown in FIG. 8.

The invention claimed is:

1. A process for preparing a cross-linked hyaluronic acid product, comprising the step of cross-linking a hyaluronic acid using an enantioenriched mixture of BDDE stereoisomers, wherein one of the following enantiomers of BDDE is present in a percentage share of at least 50%:

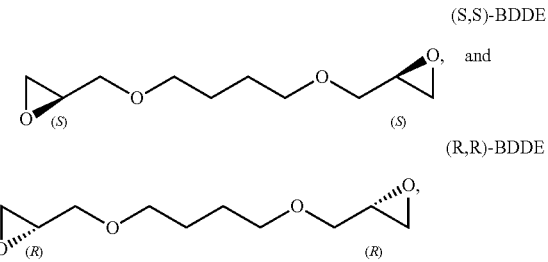

as cross-linking agent.

2. A cross-linked hyaluronic acid product, wherein the product is produced by cross-linking a hyaluronic acid with an enantioenriched mixture of BDDE stereoisomers according to the process of claim 1.

3. A cross-linked product according to claim 2, wherein the cross-linked product is cross-linked via ether bonds to the BDDE.

4. A cross-linked product according to claim 2, wherein the cross-linked product is cross-linked via ester bonds to the BDDE.

5. A cross-linked product according to claim 2, wherein the cross-linked product is cross-linked via a mixture of ether and ester bonds to the BDDE.

6. A cross-linked product according to claim 2, wherein the cross-linked product is a gel.

7. A cross-linked product according to claim 2, wherein the cross-linked product is a dermal filler product.

* * * * *